United States Patent [19]

Hurd et al.

[11] Patent Number: 4,818,360
[45] Date of Patent: Apr. 4, 1989

[54] METHOD AND APPARATUS FOR BLOTTING FROM ELECTROPHORESIS GELS

[75] Inventors: Stanley M. Hurd, Hamden; Richard E. Kouri, New Haven, both of Conn.

[73] Assignee: Bios Corporation, New Haven, Conn.

[21] Appl. No.: 90,740

[22] Filed: Aug. 28, 1987

[51] Int. Cl.$^4$ .................. G01N 27/26; G01N 27/28
[52] U.S. Cl. ..................... 204/299 R; 204/182.8; 204/180.1
[58] Field of Search ............ 204/182.8, 182.9, 180.1, 204/299 R

[56] References Cited

PUBLICATIONS

Michael H. Johnson et al., "Identification of Protein Bands in Polyacrylaminde Gel by Protein Printing", Biochemica et Biophysica Acta 718, (1982), 121–124, Elsevier Biomedical Press.

*Primary Examiner*—John F. Niebling
*Assistant Examiner*—John S. Starsiak, Jr.
*Attorney, Agent, or Firm*—Bachman & LaPointe

[57] ABSTRACT

A rapid and effective method and apparatus or blotting is provided whereby a relatively thin gel slab containing electrophoresed, electrostatically charged material is transferred to a porous membrane of opposite charge by means of simple electrostatic attraction free of any external influence or inducement.

4 Claims, 1 Drawing Sheet

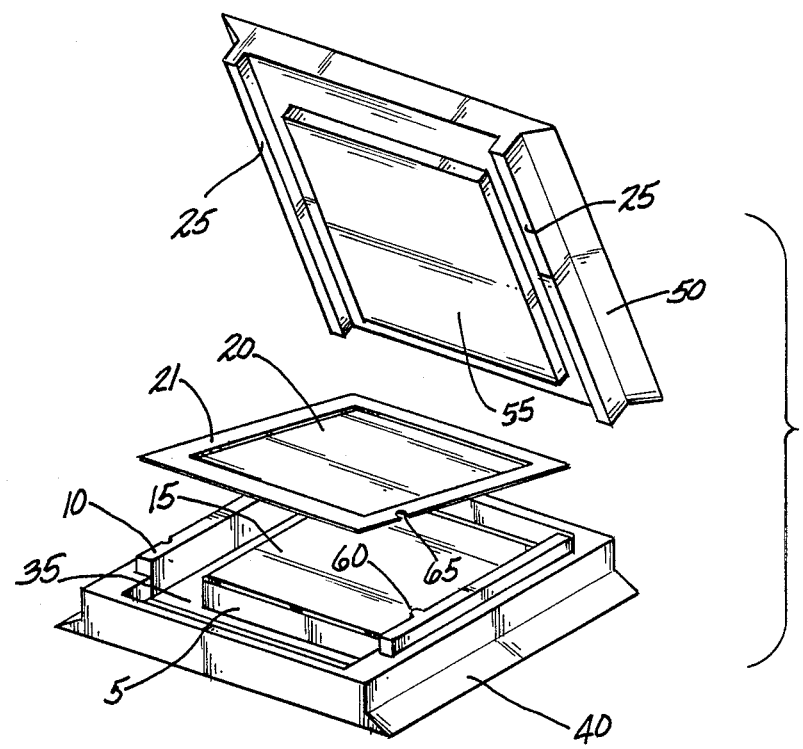

METHOD AND APPARATUS FOR BLOTTING FROM ELECTROPHORESIS GELS

RELATED APPLICATION

An application filed as of even date by Hurd et al. entitled BLOT FRAME AND METHOD OF HANDLING, Ser. No. 090739 filed 8-28-87.

BACKGROUND OF THE INVENTION

The present invention describes a device and a procedure which are used routinely in the study of macromolecules: i.e. the transfer of electrophoresed species to thin membrane sheets, commonly called blotting.

It is the general object of the present invention to provide an improved method and apparatus to carry out blotting of biological components. The basis of the invention is a novel blotting procedure and apparatus which requires thin, low concentration gels for maximum effectiveness. Such gels are made possible and practical by the horizontal electrophoresis gel tray mold assembly described in a co-pending application Ser. No. 051,761 filed May 20, 1987 by Hurd et al. entitled A METHOD AND APPARATUS FOR MOLDING THIN GEL SLABS HORIZONTALLY WITH INTEGRALLY MOLDED LARGE VOLUME WELL SAMPLES.

The complete disclosure of said '761 application is incorporated herein by this reference to the '761 application.

Blotting is the process by which material such as DNA, RNA, proteins or the like which have been resolved electrophoretically in a gel matrix are transferred to an electrostatically charged membrane sheet in order to be visualized and analyzed.

In conventional prior art blotting procedures, species which have been separated by electrophoresis are transferred to appropriate membranes by driving the species onto the membrane electrophoretically or by drawing them out of the gel by a flow of buffer passing through both gel and membrane (see, for example, Kreisher, J. H., U.S. Pat. No. 4,589,965, 1986, and Southern, E. M. J. Mol. Biol. 98:503, 1975). The use of an electric current or buffer flows is necessitated by the fact that the electrophoretic gels are commonly 5-10 mm thick. In gels of this thickness an independent, active driving force is needed to bring the species of interest through the gel into contact with the blotting membrane.

In the most commonly used procedures, the membranes are layered on top of the gels, and then the gel and membrane together are sandwiched in the blotting apparatus. At this point the fluid or electrical current is initiated to drive the materials out of the gel and onto the membrane. These prior art procedures are time-consuming, often requiring several hours or more to complete. The electrophoretic units require costly power supplies and transfer chambers. Those techniques utilizing fluid flows as the driving force often require 20 hours or more to effect the transfer of the material to the membrane from the gel. In addition, fluid streams require large volumes of buffer in order to effect the transfer.

SUMMARY OF THE INVENTION

The present invention embodies a novel blotting procedure and apparatus which utilizes thin (ranging from less than 2 mm to 0.05 mm) gels and passive transfer of the materials in the gels to the blotting membrane. This procedure has the benefits of being significantly faster than the fluid-flow techniques, while it is significantly less expensive than the electroblotting techniques and compares favorably with electroblotting in the time required to effect transfer.

It is therefore an object of the present invention to provide a means by which materials separated by electrophoretic processes may be transferred to blotting membranes without the use of externally applied electrical current or fluid flows.

It is another object of the present invention to provide a means by which gels of low concentration and of thin cross sections can be blotted.

It is a further object of the present invention to minimize the amount of handling of the gels required during the blotting procedure.

A further feature of the invention is the provision of an inexpensive, rapid process for transferring electrophoretically resolved material from a thin gel slab to a blotting membrane with high quality pattern resolution.

A still further feature of the invention is the provision of a "passive" membrane blotting procedure, i.e. free of an induced electric field or other driving force of external origin.

A further feature of the invention is the provision of a novel apparatus for effecting an electrostatic transfer of electrophoresed material from a thin gel slab to a membrane.

The language "thin gel" is intended to denote horizontal gel slabs having a thickness ranging from 0.05 mm to less than 2 mm.

A further feature of the invention is the provision of a blotting procedure that is practiced while the gel remains upon the surface upon which the gel was molded.

These and other objects are met by the device and procedure described herein.

DESCRIPTION OF THE DRAWINGS

Single FIG. 1 comprises an exploded view of the blotting device showing the electrophoresis gel and gel tray in relation to the blot membrane.

DESCRIPTION OF THE INVENTION

As stated previously, sample species which have been separated electrophoretically often must be transferred to a permanent support matrix in order to be analyzed further. Such a matrix usually takes the form of a porous membranous sheet of material selected from the group consisting of nylon, nitrocellulose, nylon-backed nitrocellulose or the like. This transfer process is called blotting. The underlying principle in blotting according to the present invention is the attachment of the charged species in the gel to the oppositely-charged membrane by simple electrostatic attraction, i.e. free of an induced electric field or other external force. Sample species in direct apposition to the membrane (i.e., those lying at or very near the gel surface) are attracted to the membrane and bind to it firmly. However, since the species are large relative to the pore size of the gels commonly used, they do not readily diffuse through it. Therefore, those species lying too far below the surface of the gel do not transfer to the membrane in the absence of some driving force. Since most prior art gels are commonly rather thick (5 mm to 10 mm) in order to withstand handling, the bulk of the materials within them will not transfer to the membranes passively. This is the reason for the use of electric current or fluid flow in prior art procedures to carry the species out of thick gels onto the membrane.

It is possible, however, to construct gels that are significantly thinner, ranging from less than 2 mm to 0.05 mm, and of less concentrated formulation than are normally used in current or prior art procedures. As stated previously, the preparation of said thin gel slabs is described in co-pending '761 application.

The benefits of faster and cooler electrophoresis runs which result from such thin gels, have been sought continuously by those skilled in the art. The use of thin gels makes possible blotting of the gels without the use of any electrical field or fluid flow as a driving force. This type of blotting, termed passive blotting is, in fact, the only practical way to carry out blotting on gels less than 2 mm thick, because the gel can remain on the gel ray on which the gel was molded throughout the procedure. If such a delicate gel were to be removed and placed into a conventional blotting apparatus, the necessary handling would almost certainly tear or otherwise mutilate a gel of such thinness. This obviously would have a deleterious effect on the resulting blot.

FIG. 1 shows a preferred embodiment of a device for carrying out passive blotting. In this embodiment, gel tray 10, with a thin gel 15 resting on elevated platform or plate 5 thereof is securely but releasably socketed in base unit 40 (the gel tray and its use in the gel molding steps are described fully in co-pending '761 application). These members such as tray 10, platform 5 and base unit 40 are constructed of a rigid, inert material, such as acrylic plastic.

Framed blot membrane 20, generally coextensive in area with the gel 15, is lowered onto the gel, preferably at an angle, initially and gradually moved into full areal contact.

The framed blot membrane interlocks with the tray 10 by the cooperation between the protuberance 60 and the cut-out 65 in the manner described in said co-pending application, Ser. No. 090739, filed as of even date herewith.

Next the top unit 50 of the blotting device is then lowered onto the upper surface of membrane 20 such that elevated surface or top plate 55 of top unit 50 presses the membrane firmly against the gel.

A benefit of top unit 50 pressing and holding a framed membrane is derived from the fact that it is an absolute requirement that the membrane remain fixed relative to the gel once the membrane and the gel are placed in contact with one another. The sample species in the surface layers of the gel migrate very quickly to the membrane after contact. Any shifting of the membrane relative to the gel after initial contact will result in a blurred blot which is difficult to interpret. The pressure created by the top unit 50 eliminates the shifting problem.

It is to be noted that the area of the top plate 55 corresponds to the area of the membrane within the frame 21 so that the plate 55 and the surface of the membrane within the frame are in intimate face to face contact.

For purposes of claiming the invention the top unit 50 is defined as a weight means.

The angular approach of the membrane and the weight of the top unit 50 ensure that there are no air pockets trapped between the gel and membrane surfaces when the gel, membrane and top plate 55 are assembled. Moreover, it has been observed that the blotting efficiencies are lower when no pressure is applied.

This method of blotting is faster than conventional techniques, requiring less than 25% of the time needed for most common electrophoreric transfer procedures, and is less expensive because it requires no power supply or buffer. In addition, the labor time necessary to set up this procedure is less than 20% of that required by conventional prior art techniques. This is due to the fact that the operator need not handle the slippery and fragile gel at any time.

An additional benefit of the present invention is that it allows the steps of electrophoresis and blotting to be coordinated into an integrated system, functionally coupled through the gel tray structure of the co-pending '761 application. The secure positioning of gel tray 10 in base 40 of the blotting device provides a steady and uniform orientation of the gel during blotting. This results in much greater reproducibility from one blot to another.

In the disclosed embodiment of the blotting procedure it is necessary to provide appropriate clearance between the bottom of the depending skirt 25 and the base plane 35 so that when the gel 15, membrane 20, and top plate 55 are assembled or stacked, skirt 25 does not bottom prematurely upon the base plane.

The present invention is therefore seen to embody a device and procedure that does not utilize any externally imposed fluid or electrical currents in order to achieve transfer of sample species embedded in the electrophoresis gel onto the membrane sheet. This invention makes it possible to blot from thinner gels than can be used in current techniques. The present invention has the additional benefits of being faster than most of the prior art, and of requiring significantly less labor than any device or procedure in the prior art. The present invention further provides the benefit of functionally coupling the steps of electrophoresis and blotting into an integrated system. This system allows for greater reproducibility of the blots and greater ease of handling in carrying out these steps.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A blotting apparatus for transferring electrophoresed materials from a gel slab to a membrane comprising:
   a raised platform defining a bottom plate providing a flat surface for molding a gel slab,
   a base plane surrounding at least a portion of said platform;
   a gel slab disposed on said bottom plate containing a pattern of electrophoresed material,
   a top unit having a top plate;
   a membrane sandwiched between and in areal contact with the gel and with the top plate whereby the electrophoresed material migrates passively to said membrane free of any external inducement.

2. The apparatus of claim 1 above in which the starting thickness of the gel slab is less than 2 mm.

3. The apparatus of claim 1 in which the top unit includes a depending locating skirt spaced vertically from the base plane.

4. The apparatus of claim 1 in which the top unit defines a weight means applying a compressive load to said gel slab.

* * * * *